United States Patent [19]

Carr

[11] 4,246,268
[45] Jan. 20, 1981

[54] NEUROLEPTIC-4-(NAPHTHYLMETHYL)-PIPERIDINE DERIVATIVES

[75] Inventor: Albert A. Carr, Cincinnati, Ohio

[73] Assignee: Richardson-Merrell Inc., Wilton, Conn.

[21] Appl. No.: 10,555

[22] Filed: Feb. 9, 1979

[51] Int. Cl.³ ............... A01K 31/445; C07D 211/32; C07D 211/22
[52] U.S. Cl. ............................ 424/267; 546/205; 546/206; 546/314; 546/343; 546/346; 546/348
[58] Field of Search .............. 546/201, 205, 206; 424/267

[56] References Cited

U.S. PATENT DOCUMENTS

| | | | |
|---|---|---|---|
| 3,795,677 | 3/1974 | Carr | 546/205 |
| 3,888,867 | 6/1975 | Carr | 546/237 |
| 4,145,427 | 3/1979 | Langbein et al. | 424/267 |

FOREIGN PATENT DOCUMENTS

| | | | |
|---|---|---|---|
| 925429 | 5/1963 | United Kingdom | 546/201 |
| 1404003 | 8/1975 | United Kingdom | 546/201 |

OTHER PUBLICATIONS

Panizzon, L., *Helv. Chim. Acta*, 27, 1751 (1944).
March, J. *Advanced Organic Chemistry*, McGraw Hill, New York, 1968, pp. 413–414.

*Primary Examiner*—Henry R. Jiles
*Assistant Examiner*—Richard A. Schwartz
*Attorney, Agent, or Firm*—Edlyn S. Simmons; George W. Rauchfuss, Jr.; L. Ruth Hattan

[57] ABSTRACT

Novel compounds of the formula

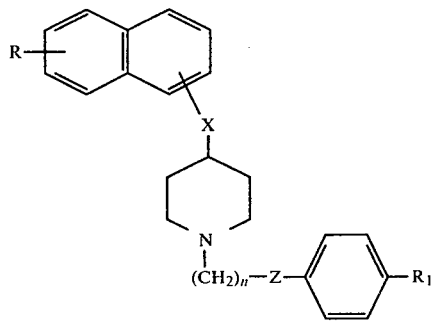

wherein n is an integer of from 2 to 5, R is hydrogen, alkyl, alkoxy, halogen or trifluoromethyl, $R_1$ is hydrogen, alkyl, alkoxy or halogen, X is carbonyl, hydroxymethylene or methylene, and Z is carbonyl or hydroxymethylene and their pharmaceutically acceptable acid addition salts are useful as antipsychotic agents having a low potential for extrapyramidal side effects. The novel compounds are prepared from novel intermediates of formula

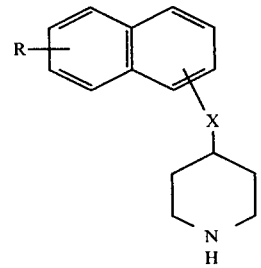

or their salts wherein R and X have the meanings defined above.

23 Claims, No Drawings

NEUROLEPTIC-4-(NAPHTHYLMETHYL)PIPERIDINE DERIVATIVES

FIELD OF THE INVENTION

This invention relates to novel derivatives of 4-(napthylmethyl)piperidines and methods for their preparation. More particularly it relates to new naphthyl 4-piperidyl ketones, α-(naphthyl)-4-piperidinemethanols, and 4-(naphthylmethyl)piperidines useful as chemical intermediates and their N-(ω-benzoylalkyl) and N-(ω-hydroxy-ω-phenylalkyl) derivatives useful as neuroleptic tranquilizers whose use does not induce significant extra-pyramidal side effects.

DESCRIPTION OF THE PRIOR ART

4-Piperidyl 1- and 2-naphthyl ketones, which are useful as analgesics and anticoagulants, are claimed in U.S. Pat. No. 3,795,677. It has now been discovered that these compounds and their alkyl-, alkoxy-, halo-, and trifluoromethylnaphthyl analogs are useful as intermediates in the preparation of new ω-[4-(naphthoyl)-1-piperidyl]-, [4-(naphthylhydroxymethyl)-1-piperidyl]- and [4-naphthylmethyl-1-piperidyl]-1-phenyl-1-alkanones and -1-phenyl-1-alkanols.

2-(1- And 2-naphthylmethyl)piperidine, the 2-piperidyl isomers of the novel 4-(naphthylmethyl)piperidines of this invention are reported to have been formed in a rearrangement reaction by Koehler, et al., *Tetrahedron Lett.* 1977(7), 635-8, and 2-(1-naphthylmethyl)piperidine has been reported to have been prepared by L. Panizzon, *Helv. Chim. Acta* 27, 1748-56 (1944). These isomers have not been disclosed as useful and are not useful as intermediates in the preparation of the novel neuroleptic tranquilizers of this invention.

SUMMARY OF THE INVENTION

Novel compounds of formula

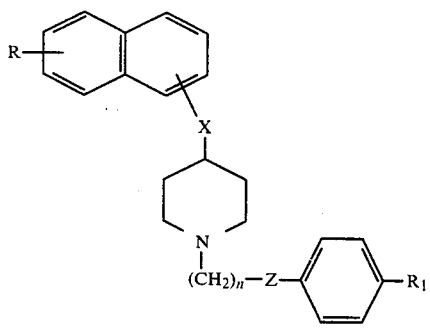

Formula I wherein n is an integer of from 2 to 5; R is hydrogen, alkyl, alkoxy, halogen or trifluoromethyl; $R_1$ is hydrogen, alkyl, alkoxy or halogen; X is carbonyl, hydroxymethylene or methylene; and Z is carbonyl or hydroxymethylene; are useful as antipsychotic agents. These antipsychotic compounds may be prepared by alkylation of intermediates of formula II

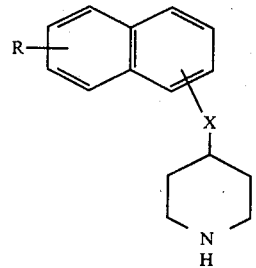

Formula II wherein R and X have the meanings defined above. With the exception of compounds wherein X is carbonyl and R is hydrogen, compounds of Formula II are also novel compounds and are included in this invention. Included in the invention are the pharmaceutically acceptable acid addition salts and individual optical isomers of the compounds of Formula I and Formula II.

DETAILED DESCRIPTION OF THE INVENTION

Compounds of Formula I include 1- and 2-naphthyl derivatives of ω-[4-(naphthoyl)-1-piperidyl]-, ω-[4-(naphthylhydroxymethyl)-1-piperidyl]-, and ω-[4-(naphthylmethyl)-1-piperidyl]-1-(4-substituted)phenyl-1-alkanones of Formula III

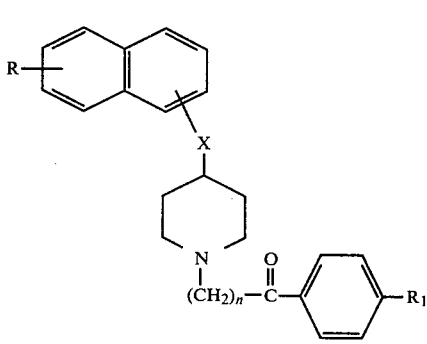

Formula III and 4-naphthoyl, 4-(naphthylhydroxymethyl)-, and 4-(naphthylmethyl)-α-(4-substituted)phenyl-1-piperidinealkanols of Formula IV

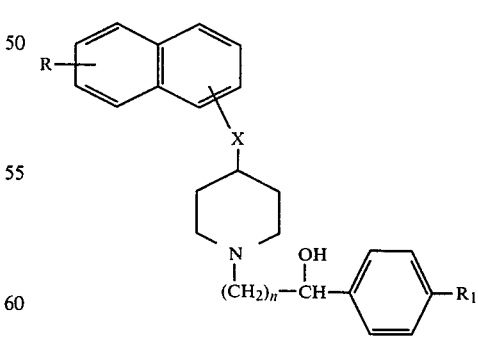

Formula IV wherein n, X, R and $R_1$ have the meanings defined above, their individual geometrical and optical isomers, and their pharmaceutically acceptable acid addition salts.

As used herein, alkyl is taken to mean straight or branched chain alkyl groups having from 1 to 4 carbon atoms. Illustrative examples of alkyl groups are methyl, ethyl, propyl and tertiary butyl. Alkoxy is taken to mean straight or branched chain alkoxy groups having from 1 to 4 carbon atoms. Illustrative examples of alkoxy groups are methoxy, ethoxy and isopropoxy. Halogen is taken to mean fluorine, chlorine or bromine.

The substituent R may be located in any position of the naphthalene ring system other than the position occupied by the (X-piperidyl) substituent.

Preferred embodiments of this invention are compounds of Formula I wherein Z is carbonyl and X is selected from carbonyl and hydroxymethylene; also preferred are embodiments of this invention wherein n is equal to 3. Further preferred embodiments of this invention are compounds of Formula I wherein R is selected from hydrogen and halogen. Preferred embodiments of this invention also include compounds of Formula I wherein $R_1$ is halogen and especially fluorine.

Exemplary compounds of Formula I are
4-[4-(1-naphthoyl)-1-piperidyl]-1-(4-fluorophenyl)-1-butanone,
4-[4-(2-naphthoyl)-1-piperidyl]-1-(4-fluorophenyl)-1-butanone,
4-[4-(6-chloro-2-naphthoyl)-1-piperidyl]-1-(4-fluorophenyl)-1-butanone,
3-[4-(4-methoxy-1-naphthoyl)-1-piperidyl]-1-(4-chlorophenyl)-1-propanone,
4-[4-(2-naphthoyl)-1-piperidyl]-1-(4-methylphenyl)-1-butanone,
5-[4-(1-methyl-2-naphthoyl)-1-piperidyl]-1-(4-ethoxyphenyl)-1-pentanone,
4-[4-((1-naphthyl)hydroxymethyl)-1-piperidyl]-1-(4-methylphenyl)-1-butanone,
4-[4-((2-naphthyl)hydroxymethyl)-1-piperidyl]-1-(4-fluorophenyl)-1-butanone,
3-[4-((1-fluoro-2-naphthyl)hydroxymethyl)-1-piperidyl]-1-(4-fluorophenyl)-1-propanone,
3-[4-((8-methoxy-2-naphthyl)hydroxymethyl)-1-piperidyl]-1-phenyl-1-propanone,
4-[4-((1-naphthyl)methyl)-1-piperidyl]-1-(4-fluorophenyl)-1-butanone,
4-[4-((6-chloro-2-naphthyl)methyl)-1-piperidyl]-1-(4-chlorophenyl)-1-butanone,
6-[4-((2-naphthyl)methyl)-1-piperidyl]-1-(4-methylphenyl)-1-hexanone,
4-[(1-naphthyl)hydroxymethyl]-α-(4-fluorophenyl)-1-piperidinebutanol,
4-[(4-trifluoromethyl-2-naphthyl)hydroxymethyl]-α-(4-fluorophenyl)-1-piperidinebutanol,
4-[(6-chloro-2-naphthyl)hydroxymethyl]-α-phenyl-1-piperidinepropanol,
4-[(7-isopropyl-1-naphthyl)hydroxymethyl]-α-(4-chlorophenyl)-1-piperidinepentanol,
4-(2-naphthoyl)-α-(4-fluorophenyl)-1-piperidinebutanol,
4-(4-bromo-1-naphthoyl)-α-phenyl-1-piperidinebutanol,
4-(8-methyl-1-naphthoyl)-α-(4-chlorophenyl)-1-piperidinepropanol,
4-(6-chloro-2-naphthoyl)-α-(4-fluorophenyl)-1-piperidinebutanol,
4-[(1-naphthyl)methyl]-α-(4-fluorophenyl)-1-piperidinebutanol,
4-[(4-trifluoromethyl-2-naphthyl)methyl]-α-(4-methylphenyl)-1-piperidinebutanol,
4-[(7-isopropyl-1-naphthyl)methyl]-α-(4-methoxyphenyl)-1-piperidinepentanol, and
4-[(3-ethoxy-2-naphthyl)methyl]-α-phenyl-1-piperidinepropanol.

The invention also includes the pharmaceutically acceptable acid addition salts of compounds of Formula I, which are also active as antipsychotics. Suitable salts include those of inorganic acids, such as, hydrochloric, hydrobromic, sulfuric and phosphoric acids; carboxylic acids, such as, acetic, propionic, glycolic, lactic, pyruvic, malonic, succinic, fumaric, malic, tartaric, citric, ascorbic, maleic, hydroxymaleic, dihydroxymaleic, benzoic, phenylacetic, 4-aminobenzoic, 4-hydroxybenzoic, anthranilic, cinnamic, salicylic, aminosalicyclic, 2-phenoxybenzoic, 2-acetoxybenzoic and mandelic acids; and sulfonic acids, such as, methanesulfonic, 2-hydroxyethanesulfonic and p-toluenesulfonic acids.

The novel compounds of Formula I are antipsychotic agents useful when administered alone or in the form of pharmaceutical preparations containing the novel compounds in combination with a pharmaceutical carrier as neuroleptic tranquilizers in warm blooded animals. Neuroleptic tranquilizers are useful for treatment of patients showing symptoms of psychoses, such as schizophrenia, or of severe anxiety, agitation or aggressiveness. Such agents have a tranquilizing effect on psychomotor activity, inducing a state of general quiescence in the patient without inducing sleep. Patients suitable for treatment with antipsychotic compositions containing compounds of Formula I include warm blooded animals such as birds, for example turkeys and chickens, and mammals, for example mice, rats, dogs, cats, horses, pigs, cattle, sheep and humans.

Pharmaceutical compositions containing compounds of Formula I may be in solid or liquid form, such as tablets, capsules, powders, solutions, suspensions or emulsions, and may be administered orally, parenterally, for example, intraperitoneally, intramuscularly or subcutaneously, or topically, for example, transdermally or transmucosally. The quantity comprising an effective amount of the novel compound provided in a unit dosage and the nature and quantity of the pharmaceutical carrier will vary widely according to the type of pharmaceutical composition and the body weight of members of the patient population to be treated. The treatment of a patient in need of tranquilizing will provide from 0.005 to 100 mg/kg of body weight of the patient per day to achieve the desired tranquilizing effect. For a human patient this degree of tranquilization may be achieved by means of an antipsychotic composition in the form of tablets containing from 0.5 to 300 mg of the active compound and an appropriate pharmaceutical carrier taken from 1 to 4 times a day. Smaller unit dosages will be required to achieve a comparable neuroleptic effect in smaller species of animals.

The compounds of general Formula I, together with suitable pharmaceutical carriers, can be in the form of solid unit dosage forms such as tablets, capsules and powders, in the form of a suppository, or embedded in a polymeric matrix. In the preparation of solid unit dosage forms it may be desirable to micronize the compound to be employed. In solid unit dosage forms the compounds can be combined with conventional carriers, for example, binders, such as acacia, corn starch or gelatin; disintegrating agents, such as corn starch, guar gum or alginic acid; lubricants, such as stearic acid or magnesium stearate; and inert fillers, such as lactose, sucrose or corn starch.

The compounds of general Formula I may also be administered as liquid suspensions or solutions using a sterile liquid, such as an oil, water, an alcohol or mixtures thereof, with or without the addition of a pharmaceutically suitable surfactant, suspending agent, or emulsifying agent, for oral, topical or parenteral administration.

For liquid preparations, the compounds of Formula I can be formulated suitably with oils, for example, fixed oils, such as peanut oil, sesame oil and olive oil; fatty acids, such as oleic acid and isostearic acid; and fatty acid esters, such as isopropyl myristate and fatty acid glycerides; with alcohols, such as ethanol, isopropanol and propylene glycol; with petroleum hydrocarbons; with water; or with mixtures thereof.

Peanut oil and sesame oil are particularly useful in preparation of formulations for intramuscular injection. Oils can also be employed in the preparation of formulations of the soft gelatin type and suppositories. Water, saline, aqueous dextrose and related sugar solutions and glycerols, such as polyethyleneglycol, may be employed in the preparation of liquid formulations which may suitably contain suspending agents, such as pectin, carbomers, methyl cellulose, hydroxypropyl cellulose or carboxymethyl cellulose, as well as buffers and preservatives.

Illustratively, when 4-[4-(2-naphthoyl)-1-piperidyl]-1-(4-fluorophenyl)-1-butanone hydrochloride was administered intraperitoneally to mice at a dosage of 0.3 mg/kg the aggregate toxicity of d-amphetamine was inhibited in 50% of the mice tested according to the procedures disclosed by J. Burn et al., *Arch. Int. Pharmacodyn.* 113, 290-5 (1955), thus demonstrating antipsychotic effectiveness, whereas a dosage level of 1.0 mg/kg of the known tranquilizer chlorpromazine is required to attain a similar level of response. Similarly, compounds of this invention evince neuroleptic activity through the inhibition of pernicious preening in mice tested according to the method disclosed by A. Kandel et al., *Fed. Proc.*, 19 (1, Pt. 1), 24 (1960).

The neuroleptic potency of these compounds is accompanied by a reduced tendency to produce extrapyramidal side effects in patients treated with a neuroleptically effective dosage as compared with known antipsychotic agents. Indicative of the reduced extrapyramidal effect of the compounds of this invention, when 4-[4-(2-naphthoyl)-1-piperidyl]-1-(4-fluorophenyl)-1-butanone hydrochloride was administered intraperitoneally to mice, a dosage of 16.6 mg/kg was required to counteract the behavioral effects of apomorphine in 50% of the mice tested according to the general method disclosed by P. A. J. Janssen et al., in *Arzneim-Forsch.* 10, 1003 (1960), whereas only 1.4 mg/kg of chlorpromazine was required to attain a similar effect.

Compounds of Formula I are prepared by alkylation of intermediate compounds of Formula II. Compounds of Formula II, with the exception of 1- and 2-naphthyl 4-piperidyl ketone, that is of compounds of Formula II wherein X is carbonyl and R is hydrogen, are also new and represent a part of this invention.

Compounds of Formula II include 1- and 2-naphthyl 4-piperidyl ketones of Formula V

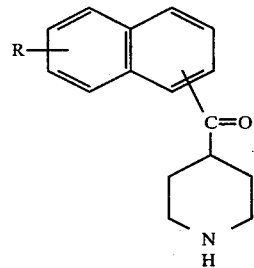

Formula V

α-(1- and 2-naphthyl)-4-piperidinemethanols of Formula VI

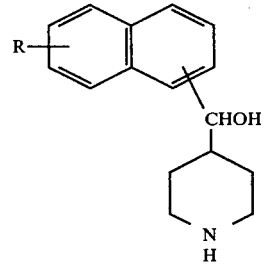

Formula VI and their individual optical isomers, and 4-[(1- and 2-naphthyl)methyl]piperidines of Formula VII wherein R has

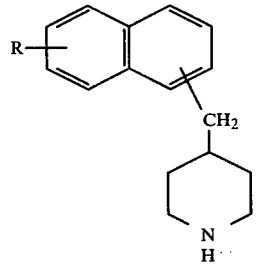

Formula VII the meaning defined above, and acid addition salts thereof.

Exemplary compounds of Formula II include
1-naphthyl 4-piperidyl ketone,
2-naphthyl 4-piperidyl ketone,
6-chloro-2-naphthyl 4-piperidyl ketone,
4-methoxy-1-naphthyl 4-piperidyl ketone,
1-methyl-2-naphthyl 4-piperidyl ketone,
1-fluoro-2-naphthyl 4-piperidyl ketone,
8-methoxy-2-naphthyl 4-piperidyl ketone,
4-trifluoromethyl-2-naphthyl 4-piperidyl ketone,
7-isopropyl-1-naphthyl 4-piperidyl ketone,
α-(1-naphthyl)-4-piperidinemethanol,
α-(2-naphthyl)-4-piperidinemethanol,
α-(6-chloro-2-naphthyl)-4-piperidinemethanol,
α-(4-methoxy-1-naphthyl)-4-piperidinemethanol,
α-(1-methyl-2-naphthyl)-4-piperidinemethanol,
α-(1-fluoro-2-naphthyl)-4-piperidinemethanol,
α-(8-methoxy-2-naphthyl)-4-piperidinemethanol,
α-(4-trifluoromethyl-1-naphthyl)-4-piperidinemethanol,
α-(7-isopropyl-1-naphthyl)-4-piperidinemethanol,
4-[(1-naphthyl)methyl]piperidine,
4-[(2-naphthyl)methyl]piperidine,
4-[(6-chloro-2-naphthyl)methyl]piperidine, 4-[(4-methoxy-1-naphthyl)methyl]piperidine,
4-[(1-methyl-2-naphthyl)methyl]piperidine,
4-[(1-fluoro-2-naphthyl)methyl]piperidine,
4-[(8-methoxy-2-naphthyl)methyl]piperidine,
4-[(4-trifluoromethyl-1-naphthyl)methyl]piperidine, and
4-[(7-isopropyl-1-naphthyl)methyl]piperidine.

Compounds of Formula Va, wherein $R_2$ is selected from hydrogen, halogen, alkyl and alkoxy and, when $R_2$ is other than hydrogen, wherein $R_2$ is bonded to the 2, 4 or 7 position of the naphthalene skeleton when the 4-piperidylcarbonyl group is in the 1-position and $R_2$ is bonded to the 6-position of the naphthalene skeleton when the 4-piperidylcarbonyl group is in the 2-position, may be prepared directly by the Friedel-Crafts acylation of an appropriate naphthalene derivative by the hydrohalide salt of a 4-piperidinecarbonyl halide as illustrated by the following:

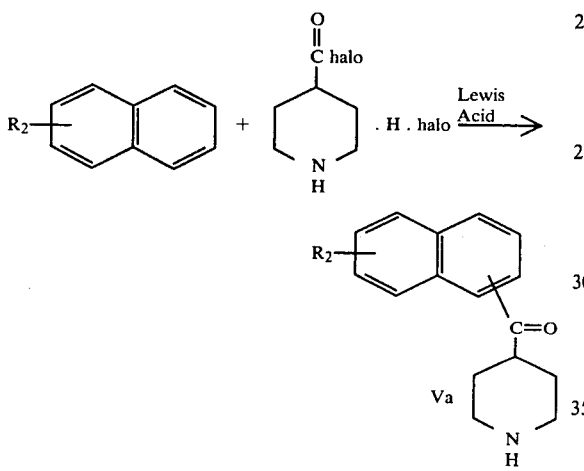

wherein halo represents a chlorine or bromine atom.

When a 1-substituted naphthalene derivative is subjected to the Friedel-Crafts reaction, the predominant product is a 1,4-disubstituted product. When a 2-substituted naphthalene derivative is subjected to the Friedel-Crafts reaction, the predominant product is a 1,2-, 2,6- or 1,7-disubstituted product. The proportions of the various isomers of compounds of Formula Va, including the proportions of otherwise unsubstituted 1- and 2-naphthyl 4-piperidyl ketones may be varied by varying the reaction conditions, as generally described by P. H. Gore in *Friedel-Crafts and Related Reactions*, vol. III (G. A. Olah, Ed., Interscience Publishers) p. 1–382 (1964).

The above reaction may be carried out in a variety of solvents, such as nitrobenzene, chloronated hydrocarbons, for example, chloroform and tetrachloroethane, or carbon disulfide, and under catalysis of a variety of Lewis acids, such as aluminum chloride, boron trifluoride, hydrofluoric acid or stannic chloride. The amount of Lewis acid employed in the reaction varies on a molar basis from 1 to 8 times and is preferably 3 to 4 times more than the amount of the 4-piperidinecarbonyl halide. A preferred procedure is to combine the reactants, in the presence of a solvent in an ice bath, slowly adding an excess of aluminum chloride with stirring, maintaining the temperature below 35° C. After the addition is complete the temperature is elevated to from 25° to 90° C., preferably 50° to 70° C. for from 10 minutes to 6 hours, preferably 10 to 30 minutes. The reaction mixture is decomposed with water and ice and then made strongly alkaline by treating with cooling with a 50% solution of sodium hydroxide. The basified reaction mixture is then extracted with a suitable solvent, such as toluene chloroform or chlorobenzene. The organic extract is dried, filtered and concentrated to give a base of Formula Va, which may be converted to an acid addition salt by reacting a suitable acid with the base according to generally known procedures.

The corresponding α-(naphthyl)-4-piperidinemethanols of Formula VIa and 4-naphthylmethylpiperidines of Formula VIIa may be prepared by selectively reducing the ketones of Formula Va prepared by the above-described method. For catalytic reduction, a ketone of Formula Va may, for example, be dissolved in a solvent, such as acetic acid, ethyl acetate, or a lower aliphatic alcohol, such as methanol or isopropanol, and the solution agitated in the presence of hydrogen at from about 1 to about 4 atmospheres of pressure and room temperature, that is about 20°–25° C., in the presence of a suitable catalyst and at least one equivalent of an acid until the theoretical molar amount of hydrogen gas is taken up. Under mild conditions such as when the catalyst is selected from platinum, platinum oxide and rhodium, one equivalent of hydrogen will be absorbed and the corresponding alcohol of Formula VIa will be produced. Under stronger conditions, such as when the catalyst is selected from palladium and copper chromium oxide, a strong acid, such as hydrochloric, sulfuric or perchloric acid is added, and the reaction temperature is optionally raised to a temperature in the range from 25° to 100° C., 2 equivalents of hydrogen gas will be absorbed and a 4-naphthylmethylpiperidine of Formula VIIa produced.

Alternatively, the ketone of Formula Va may be selectively reduced by reaction with a suitable chemical reducing agent. When the ketone is refluxed in ether for from 1 to 5 hours with a metal hydride, for example, lithium aluminum hydride or diborane, or is reacted for from about ½ to 8 hours at a temperature of from 0° C. to the reflux temperature of a lower aliphatic alcohol solvent, such as methanol or ethanol, with a metal borohydride, such as sodium borohydride or potassium borohydride an α-(naphthyl)-4-piperidinemethanol of Formula VIa will be produced. A 4-(naphthylmethyl)-piperidine of Formula VIIa may be prepared by refluxing the ketone of Formula Va for from 1 to 4 hours with zinc amalgam in the presence of from about 2 to about 10 equivalents of hydrochloric acid, wherein the hydrochloric acid is supplied as dry hydrogen chloride in an aprotic organic solvent, such as ether or benzene, or as a concentrated aqueous solution in the presence of an organic solvent or by heating the ketone of Formula Va for from 2 to 10 hours at a temperature of from about 90° to about 200° C. with hydrazine hydrate and a strong base, for example, an alkali metal alkoxide, such as sodium ethoxide or an alkali metal hydroxide, such as potassium hydroxide, and optionally a platinum metal catalyst, followed by the usual workup.

Additional reagents suitable for the selective reduction of a ketone to an alcohol or to an alkane will be obvious to one skilled in the art. The reduced bases of Formula VIa and Formula VIIa may be converted to acid addition salts by reaction with a suitable acid according to generally known procedures.

The general method for the Friedel-Crafts preparation of compounds of Formula II wherein $R_2$ is hydrogen, halogen, alkyl or alkoxy and, when $R_2$ is other than hydrogen,

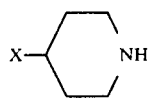

and $R_2$ are bonded to the 1, 4; 1, 2; 2, 6; or 1, 7 positions of the naphthalene ring is illustrated by general reaction Scheme A.

pyridinecarbonitrile yields a naphthyl 4-pyridyl ketone, 4; the reaction of a naphthyl Grignard reagent of structure 1 with 4-pyridinecarboxaldehyde yields an α-(naphthyl)-4-pyridinemethanol, 5; and the reaction of a naphthyl Grignard reagent of structure 1 with a 4-halomethylpyridine yields a 4-(naphthylmethyl)pyridine, 3. The relative positions of the R- and pyridylmethyl-substituents in compounds of structure 3, 4 and 5 are the same as those of the R- and halogen substituents of the compound of structure 2 from which the Grignard reagent is prepared.

Reaction Scheme A - Friedel-Crafts
Synthesis of Compounds of Formula II

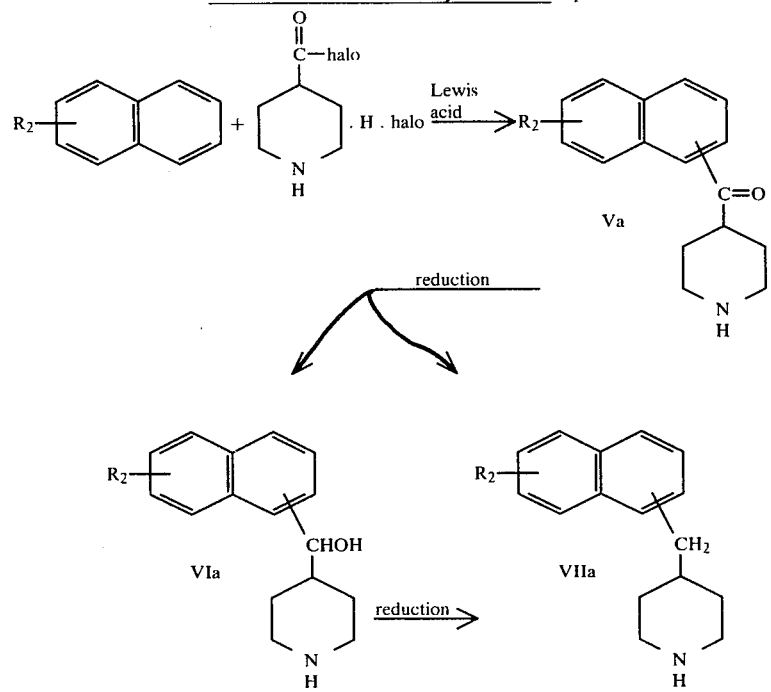

Each of the compounds of Formula II may be prepared by means of reactions of the Grignard reagents, 1, formed by the reaction with magnesium metal of bromo- and iodonaphthalenes of structure 2,

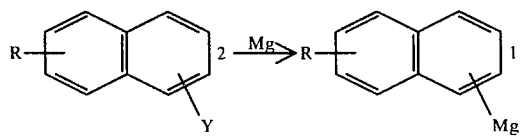

wherein R has the meaning hereinabove defined and Y is bromine or iodine. Compounds of structure 2 are well known in the art and may be prepared by well known methods. The naphthyl halide, 2, is stirred at reflux temperature with magnesium powder or turnings in an ether solvent, such as ethyl ether or tetrahydrofuran, and optionally a catalyst, such as iodine, for from 1 to 16 hours. A pyridine derivative selected from 4-pyridinecarbonitrile, 4-pyridinecarboxaldehyde and 4-halomethylpyridine is added to the resulting Grignard reagent and the mixture is refluxed for from 2 to 8 hours and the resulting adduct decomposed by addition of a cold, dilute aqueous mineral acid solution or, preferably, a saturated aqueous ammonium chloride solution. As illustrated in Reaction Scheme B, the reaction of a naphthyl Grignard reagent of structure 1 with 4-

The pyridyl compounds are selectively reduced catalytically to yield from 4-(naphthylmethyl)pyridines of structure 3, 4-(naphthylmethyl)piperidines of Formula VII, and from naphthyl pyridyl ketones of structure 4 and α-(naphthyl)-4-pyridinemethanols of structure 5 either α-(naphthyl)-4-piperidinemethanols of Formula VI or 4-(naphthylmethyl)piperidines of Formula VII, depending upon the chosen reaction conditions. Catalytic reduction under mild conditions, as described above, produces compounds of Formula VII from 4-(naphthylmethyl)pyridines with the consumption of 3 equivalents of hydrogen gas and compounds of Formula VI from α-(naphthyl)-4-pyridinemethanols with the consumption of 3 equivalents of hydrogen gas or from naphthyl 4-pyridyl ketones with the consumption of 4 equivalents of hydrogen gas. Catalytic reduction under the stronger conditions described above yields 4-(naphthylmethyl)piperidines of Formula VII from α-(naphthyl)-4-pyridinemethanols with the consumption of 4 equivalents of hydrogen gas or from naphthyl 4-pyridyl ketones with the consumption of 5 equivalents of hydrogen gas. Alternatively, an α-(naphthyl)-4-piperidinemethanol of Formula VI prepared as described hereinabove may be dehydrated by refluxing its alcoholic solution for from about 6 to about 24 hours with an aqueous solution of a strong acid, such as hydrochloric, sulfuric or phosphoric acid, adjusting the pH of the solution to about 10 with 10% sodium hydroxide, extracting the dehydrated intermediate, 6, into an organic solvent and, after evaporation of the solvent, reducing the dehydrated intermediate catalytically under mild conditions, as described above, consuming 1 equivalent of hydrogen gas, to give a compound of Formula VII, as illustrated below:

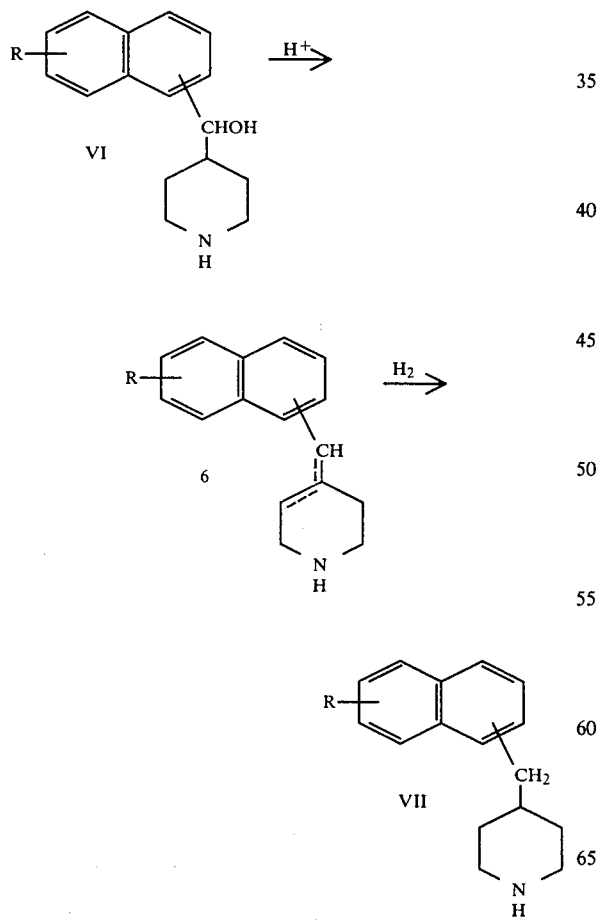

When a naphthyl piperidyl ketone of Formula V is to be prepared, the α-(naphthyl)-4-piperidinemethanol of Formula VI is oxidized by reaction with a suitable oxidizing agent, according to methods well known in the art. Oxidizing agents capable of converting a secondary alcohol of Formula VI to a ketone of Formula V include, for example, chromic acid, chromic anhydride, sodium dichromate and lead tetraacetate in a suitable solvent, such as acetic acid, sulfuric acid or pyridine, and potassium permanganate and manganese dioxide in a suitable solvent, such as petroleum ether, benzene, methylene chloride or water. The temperature of the reaction may vary from 0° to 100° C., and is preferably at room temperature. The reaction time may vary from 10 minutes to one day, and is preferably from ½ to 1 hour.

A naphthyl methyl piperidine of Formula VII may be converted to a piperidinemethanol of Formula VI, for example, by base-catalyzed hydroxylation with molecular oxygen according to the general procedures disclosed by J. Gutzwiller et al., in J. Am. Chem. Soc. 92, 204-5 (1970).

Naphthyl 4-piperidyl ketones of Formula V may also be obtained by reaction of a naphthyl Grignard reagent of structure 1 with 4-piperidinecarbonitrile or its N-protected derivative, such as N-acetyl-4-piperidinecarbonitrile or N-trifluoroacetyl-4-piperidinecarbonitrile, under the conditions described above, with the additional step of hydrolyzing the product to remove the nitrogen protecting group. Naphthyl 4-piperidyl ketones of Formula V prepared in this manner may also be reduced selectively to prepare the α-(naphthyl)-4-piperidinemethanols of Formula VI and the 4-(naphthylmethyl)piperidines of Formula VII.

The general method of preparing intermediate compounds of Formula II by means of a Grignard reagent is illustrated by general reaction Scheme B, wherein Q is CN, CHO or CH₂-halo, R₃ is H or a protecting group, and R has the meaning defined above.

Reaction Scheme B
Grignard Synthesis of Compounds of Formula II

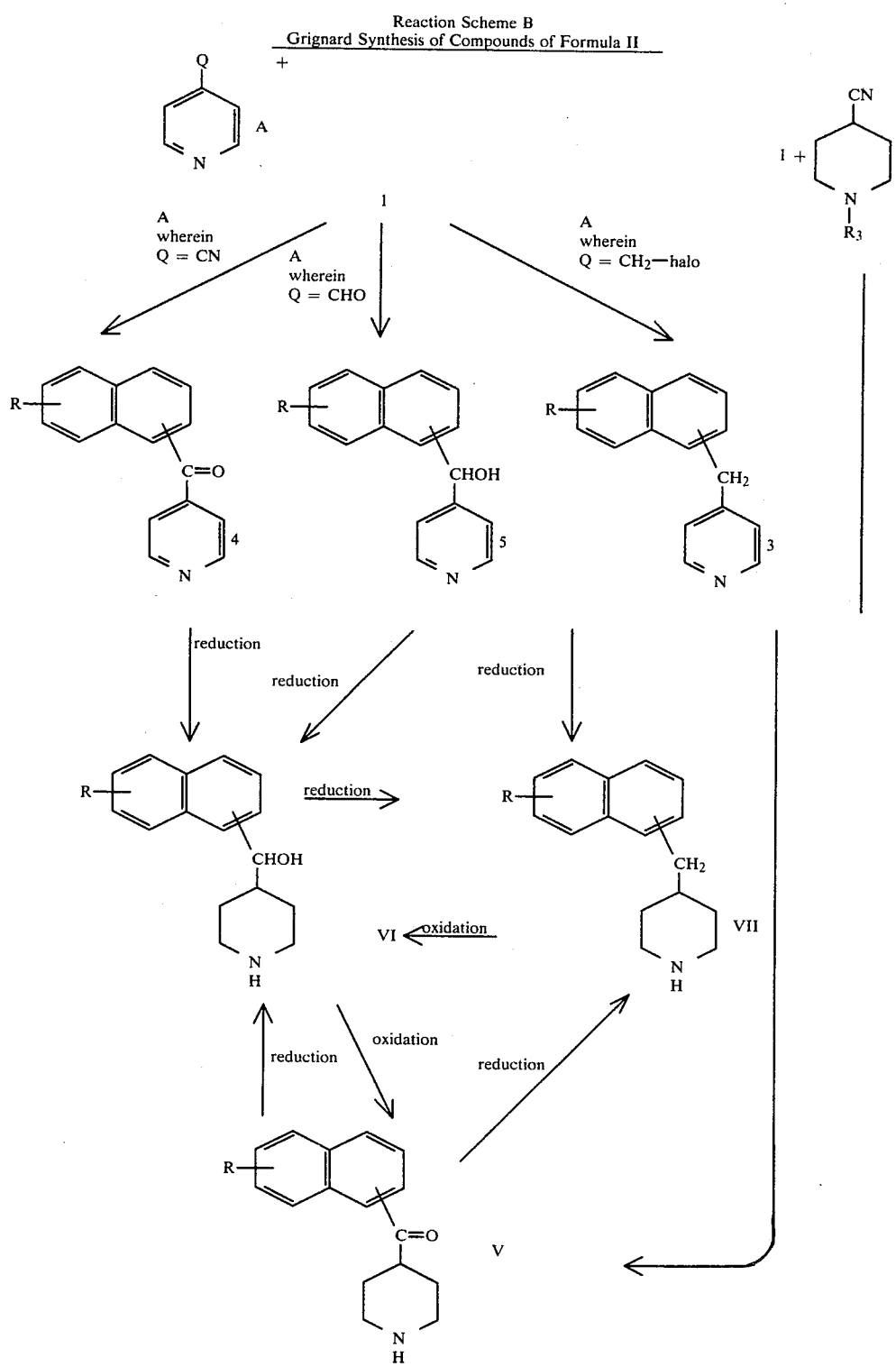

4-(Naphthylmethyl)pyridines of structure 3, naphthyl 4-pyridyl ketones of structure 4 or α-(naphthyl)-pyridinemethanols of structure 5 may also be prepared by other methods known in the art, for example, by oxidation of the corresponding tetralin derivative, as disclosed in G.B. Pat. No. 1,110,087, and by reaction of organometallic reagents other than the naphthyl Grignard reagents described herein, for example, by reaction of 4-lithiopyridine, as described by J. P. Wilbaut et al., Rec. Trav. Chim. 74, 1003–20 (1955) or of organosodium or organopotassium reagents, and may be selectively reduced and optionally oxidized as described above to yield compounds of Formula II.

Free bases of Formula II prepared by any of the above-mentioned methods may be converted to the acid addition salts by reaction with a suitable acid according to generally known procedures.

The compounds of Formula I are prepared by reacting a piperidine derivative of Formula II with a small excess of an ω-haloalkyl phenyl ketone or an ω-halo-1-phenyl-1-alkanol of structure 7 in the presence of an excess of an acid acceptor such as, for example, sodium bicarbonate, potassium bicarbonate, sodium carbonate or potassium carbonate, and optionally a small amount of potassium iodide in a suitable solvent. If desired, 2 or more equivalents of a piperidine derivative of Formula II relative to compound 7 may be used instead of the mineral base acid acceptor. The compounds of Formula I may also be prepared from the acid addition salt of a compound of Formula II by reacting the acid addition salt with a compound of structure 7 in the presence of at least 2 equivalents of the mineral base acid acceptor. The reaction mixture may be reacted over a wide range of temperatures. Generally, a reaction temperature of from about 20° to 180° C. is employed. The reaction is conducted over a period of from 1 to 4 days, during which time any evolved water may be collected. As examples of suitable solvents for this reaction, there may be mentioned toluene, xylene, chlorobenzene, methyl isobutyl ketone and lower aliphatic alcohols, such as ethanol, propanol and butanol.

After completion of the reaction, the product is isolated by conventional means, for example, the reaction mixture may be filtered and the solvent removed, isolating the product. Alternately, the filtrate may be treated with ethereal solution of a suitable mineral or organic acid to give the corresponding salt of the product. The crude product is filtered off, purified by recrystallization and dried. Suitable solvents for recrystallization are, for example, lower aliphatic alcohols, such as methanol, ethanol and isopropanol; ketones, such as acetone and butanone; esters, such as ethyl acetate; ethers, such as diethyl ether; and combinations thereof.

The general method for the preparation of the compounds of Formula I can be represented by the following reaction scheme

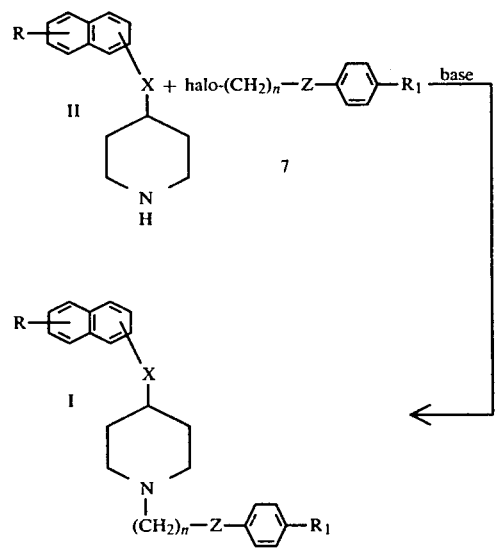

wherein n, R, R$_1$, X and Z are as hereinabove defined and halo is a reactive halogen, such as bromine, chlorine or iodine.

Compounds of Formula 7 are commercially available or may be prepared by methods well known in the art. Compounds of Formula 7 wherein Z is C=O may, for example, be prepared by reacting the appropriate ω-haloalkanoyl halide and a (substituted)benzene in the presence of a Lewis acid, such as aluminum chloride, or by reacting a (4-substituted)phenyl Grignard reagent with an appropriate ω-haloalkanonitrile. Compounds of Formula 7 wherein Z is CHOH may be prepared by reduction, by any of the means described above for reducing a ketone to an alcohol, of the corresponding 1-(4-substituted)phenyl haloalkanones of Formula 7 prepared as described above or by reaction of a (4-substituted)phenyl Grignard reagent with an appropriate ω-haloalkanaldehyde.

The compounds of Formula III wherein n is equal to 2 may also be prepared by reacting any of the compounds of Formula II with an appropriate acetophenone and formaldehyde.

1-Piperidinealkanols of Formula IV wherein X is hydroxymethylene or methylene may be prepared by reduction of alkanones of Formula III. Compounds of Formula III wherein X is hydroxymethylene or carbonyl will yield upon reduction compounds of Formula IV wherein X is hydroxymethylene; compounds of Formula III wherein X is methylene will yield compounds of Formula IV wherein X is methylene. Suitable methods of reduction include any chemical or catalytic method of reduction described hereinabove for the reduction of a ketone to an alcohol, for example, by catalytically reducing a solution of the ketone of Formula III with hydrogen gas under mild conditions in the presence of a catalyst such as platinum, platinum oxide or rhodium, or by reduction of the ketone by a metal hydride, such as lithium aluminum hydride or diborane, or a metal borohydride, such as sodium borohydride. When X is hydroxymethylene, individual disastereomers may be separated by methods, such as fractional crystallization, which are well known in the art.

Compounds of Formula I prepared in the form of free bases may be converted to their acid addition salts by reaction with a pharmaceutically acceptable acid.

The optical isomers of optically active compounds of this invention may be separated by means of any suitable resolving agent. For example, the optical isomers of compounds of Formula I or Formula II wherein one or both of X and Z is hydroxymethylene may be separated by using a (+)- or (−)-binaphthylphosphoric acid derivative or a salt of said derivative and an optically active base by the method described by R. Viterbo, et al., in *Tetrahedron Letters* 1971 (48), pp. 4617-20.

EXAMPLE 1

2-Naphthyl 4-piperidyl ketone hydrochloride

To a slurry of 99 g of naphthalene (0.75 mole) and 96 g of isonipecotic acid chloride hydrochloride (0.5 mole) in tetrachloroethane is added over a period of 10 minutes 200 g (1.5 moles) of aluminum chloride. The reaction mixture is allowed to stand at room temperature for 10 minutes, then decomposed by pouring it over ice water, made basic with a 50% NaOH solution, and extracted with diethyl ether. The ether layer is dried over magnesium sulfate, filtered, and treated with ethereal HCl. The resulting oil is dissolved in warmed methanol, treated with charcoal, filtered and diluted with butanone. The methanol is removed by distillation, adding more butanone as needed. The solution is cooled overnight, and the resulting solid filtered off and recrystallized from methanol-butanone to give the desired product. M.P. 251°–253° C.

EXAMPLE 2

1-Naphthyl 4-piperidyl ketone hydrochloride

To the mother liquor remaining after crystallization of the 2-naphthyl 4-piperidyl ketone hydrochloride in Example 1 is added a large excess of butanone. The resulting solution is reduced in volume to its approximate original volume and cooled. The resulting solid is filtered off and recrystallized from methanol/butanone to yield the 1-naphthyl isomer. M.P. 192°–194°.

EXAMPLE 3

6-Chloro-2-naphthyl 4-piperidyl ketone

To a stirred suspension of 3.15 g (19.4 mmoles) of 2-chloronaphthalene and 4.46 g (24.2 mmoles) of 4-piperidinecarbonyl chloride hydrochloride in 60 ml nitrobenzene is added gradually 9.7 g (73 mmoles) of aluminum chloride. The mixture is heated to 65°–70° C. for 2 hours and cooled. Ice water and concentrated HCl are added to the reaction mixture. The solid precipitate is partitioned between aqueous sodium hydroxide solution and ether and the organic phase washed with brine, dried over $Na_2SO_4$ and concentrated in vacuo. The residue is recrystallized from cyclohexane to yield 6-chloro-2-naphthyl 4-piperidyl ketone. M.P. 98°–100°–5°.

EXAMPLE 4

6-Chloro-2-naphthyl 4-piperidyl ketone hydrochloride

The 6-chloro-2-naphthyl 4-piperidyl ketone prepared in Example 3 is reacted with an excess of HCl dissolved in ether and recrystallized from absolute ethanol to yield 6-chloro-2-naphthyl 4-piperidyl ketone hydrochloride. M.P. 259°–64°.

EXAMPLE 5

2-Chloro-1-naphthyl 4-piperidyl ketone hydrochloride

The acidified filtrate prepared in Example 3 is extracted with ether to remove the nitrobenzene solvent and made strongly basic with NaOH. The solution is extracted with ether/benzene and the organic layer dried over $Na_2SO_4$ and concentrated in vacuo. The residue is acidified with HCl and recrystallized from butanone/methanol and from absolute ethanol to yield 2-chloro-1-naphthyl 4-piperidyl ketone hydrochloride.

EXAMPLE 6

4-Bromo-1-naphthyl 4-piperidyl ketone

When in the procedure of Example 3, 1-bromonaphthalene is substituted for 2-chloronaphthalene, 4-bromo-1-naphthyl 4-piperidyl ketone is obtained.

EXAMPLE 7

α-(1-Naphthyl)-4-piperidinemethanol hydrochloride

To a solution of 60 g (0.22 mole) of 1-naphthyl 4-piperidyl ketone hydrochloride in 500 ml of methanol, 35 g (0.65 mole) of potassium borohydride is added gradually while stirred in an ice bath and the mixture reacted for 18 hours. The mixture is concentrated in vacuo, the residue partitioned between chloroform and water, and the organic phase dried over magnesium sulfate, filtered and the solvent removed in vacuo to yield α-(1-naphthyl)-4-piperidinemethanol, which is dissolved in chloroform and an excess of dry HCl bubbled into the solution. The resulting precipitate is recrystallized from methanol/butanone to yield α-(1-naphthyl)-4-piperidinemethanol hydrochloride. M.P. 219°–21°.

EXAMPLE 8

α-(2-Naphthyl)-4-piperidinemethanol hydrochloride

When in the procedure of Example 7, 2-naphthyl 4-piperidyl ketone is substituted for 1naphthyl 4-piperidyl ketone, α-(2-naphthyl)-4-piperidinemethanol hydrochloride is obtained. M.P. 196°–8°.

EXAMPLE 9

α-(6-Chloro-2-naphthyl)-4-piperidinemethanol 3.47 g (12.7 mmoles) of (6-chloro-2-naphthyl) 4-piperidyl ketone hydrochloride is suspended in 200 ml of absolute ethanol and 1.5 g (4 mmoles) of sodium borohydride added. The reaction mixture is stirred for 18 hours and concentrated in vacuo. The residue is triturated with water and aqueous sodium hydroxide added to produce a basic solution which is extracted with toluene/methylene chloride. The organic phase is washed with brine, dried over $MgSO_4$, filtered, and concentrated in vacuo to yield α-(6-chloro-2-naphthyl)-4-piperidinemethanol.

EXAMPLE 10

α-(4-Bromo-1-naphthyl)-4-piperidinemethanol

When in the procedure of Example 9, 4-bromo-1-naphthyl 4-piperidyl ketone is substituted for 6-chloro-2-naphthyl 4-piperidyl ketone hydrochloride, α(4-bromo-1-naphthyl)-4-piperidinemethanol is obtained.

EXAMPLE 11

α-(4-Trifluoromethyl-2-naphthyl)-4-piperidinemethanol hydrochloride

To a suspension of 2.5 g (0.1 mole) of magnesium in 20 ml of tetrahydrofuran is added a crystal of iodine and a solution of 27.5 g (0.1 mole) of 1-trifluoromethyl-3-bromonaphthalene in 25 ml of tetrahydrofuran. The agitated mixture is refluxed for 1 hour, whereupon 10.7 g (0.1 mole) of 4-pyridinecarboxaldehyde dissolved in 50 ml of tetrahydrofuran is added gradually and heating continued for 3 hours. The reaction mixture is decomposed with saturated aqueous ammonium chloride solution and extracted with ether and the organic phase washed with sodium carbonate, dried over $NaSO_4$ and filtered. The ether is evaporated and the resulting α-(4-trifluoromethyl-2-naphthyl)-4-pyridinemethanol dissolved in 150 ml of acetic acid and agitated in a Parr apparatus in the presence of 1.5 g of platinum oxide. Hydrogen gas is introduced and the reaction continued until 0.3 moles of hydrogen are consumed. The mixture is filtered and the solvent removed in vacuo. Addition to the residue of an excess of HCl in ethereal solution yields α(4-trifluoromethyl-2-naphthyl)-4-piperidinemethanol hydrochloride.

EXAMPLE 12

4-Trifluoromethyl-2-naphthyl 4-piperidyl ketone hydrochloride

A chilled, stirred solution of 124 g (0.4 mole) of α-(4-trifluoromethyl-2-naphthyl)-4-piperidinemethanol hydrochloride in 600 ml of acetic acid, 40 ml of 25% sulfuric acid and 72 ml of water is added with stirring to 26.5 g (0.27 mole) of chromium trioxide in 30 ml of acetic acid over a period of 1½ hours, during which time an additional 20 ml of water is added. The mixture is stirred for ½ hour at a temperature of less than 9° C. The solvent is removed under vacuum and the residue treated with excess sodium hydroxide and extracted with ether and with chloroform. The combined extracts are washed with water, dried over MgSO$_4$ and filtered. To the filtrate is added additional chloroform and ethereal HCl. The resulting precipitate is filtered off and recrystallized from isopropyl alcohol to yield 4-trifluoromethyl-2-naphthyl 4-piperidyl ketone hydrochloride.

EXAMPLE 13

4-[(4-Trifluoromethyl-2-naphthyl)methyl]piperidine hydrochloride

When in the procedure of Example 11, palladium is substituted for platinum oxide, 4-[(4-trifluoromethyl-2-naphthyl)methyl]piperidine hydrochloride is produced.

EXAMPLE 14

α(4-Chloro-1-naphthyl)-4-piperidinemethanol hydrochloride

To a flask containing 1.8 g (72 mmoles) of magnesium turnings and 20 ml of anhydrous ether under nitrogen is added 10 drops of ethyl bromide. The ether is heated to reflux and a solution of 10 g (50 mmoles) of 1-bromo-4-chloronaphthalene in 150 ml of dry ether added gradually during 30 minutes and refluxing continued for 8 hours. 60 g (58 mmoles) of 4-pyridinecarbonitrile in 100 ml of benzene is added gradually and the solution refluxed for 3 hours and the adduct decomposed by addition of saturated ammonium chloride solution. The resulting 4-(4-chloro-1-naphthoyl)pyridine is extracted into ether and the organic phase washed with brine and dried over magnesium sulfate. The ether is removed in vacuo and the residue dissolved in methanol and reduced by reaction with 200 mmoles of hydrogen gas in the presence of a rhodium catalyst. The catalyst is filtered off, an excess of alcoholic hydrochloride acid is added, and the solution concentrated in vacuo. The residue is recrystallized from isopropanol to yield α-(4-chloro-1-naphthyl)-4-piperidinemethanol hydrochloride.

EXAMPLE 15

4-[(4-Chloro-1-naphthyl)methyl]piperidine hydrochloride

To 250 ml of 6N hydrochloric acid is added 27.6 (0.1 mole) of α-(4-chloro-1-naphthyl)-4-piperidinemethanol and enough 95% ethanol to form a clear solution. The solution is refluxed for 18 hours, cooled, and made basic with 10% sodium hydroxide, extracted into toluene, and the organic phase washed with brine, dried over MgSO$_4$, and concentrated in vacuo. The residue is dissolved in acetic acid and shaken with hydrogen gas in a Parr apparatus in the presence of 0.5 g of rhodium/carbon at room temperature until 0.1 mole of hydrogen is taken up. The catalyst is filtered off, an excess of alcoholic hydrogen chloride is added and the solution concentrated in vacuo. The residue is recrystallized from methanol to yield 4-[(4-chloro-1-naphthyl)methyl]piperidine hydrochloride.

EXAMPLE 16

8-Methyl-1-naphthyl 4-piperidyl ketone hydrochloride

A solution of 10.0 g (45 mmoles) of 1-bromo-8-methylnaphthalene in 5 ml of ethyl ether is added gradually to a stirred mixture of 1.2 g (50 mmoles) of magnesium in 30 ml of anhydrous ether. The mixture is stirred at reflux for 1 hour and a solution of 6.0 g (43 mmoles) of 1-acetyl-4-piperidinecarbonitrile in 10 ml of tetrahydrofuran slowly added. The mixture is allowed to stir for 16 hours, an excess of saturated aqueous ammonium chloride solution added and the mixture heated on a steam bath for 3 hours. After cooling, the mixtures is extracted with toluene and the organic phase dried over MgSO$_4$, filtered and concentrated in vacuo. The residue is dissolved in 20 ml of ethanol and made basic with sodium hydroxide and the solution extracted into toluene. Dry hydrogen chloride is bubbled through the organic phase to yield 8-methyl-1-naphthyl 4-piperidyl ketone hydrochloride.

EXAMPLE 17

4-[(3-Ethoxy-2-naphthyl)methyl]piperidine hydrochloride

To a suspension of 2.5 g (0.1 mole) of magnesium in 20 ml of tetrahydrofuran is added gradually a solution of 25 g (0.1 mole) of 2-bromo-3-ethoxynaphthalene in 25 ml of tetrahydrofuran. The agitated mixture is refluxed for 1 hour and a solution of 1.4 g (0.1 mole) of 4-chloromethylpyridine dissolved in tetrahydrofuran added gradually. The mixture is refluxed for 3 hours, a saturated ammonium chloride solution is added, the reaction mixture is extracted with ether, and the organic phase washed with sodium carbonate and dried over sodium sulfate. The ether is evaporated and the resulting 4-[(3-ethoxy-2-naphthyl)methyl]pyridine dissolved in acetic acid and agitated in a Parr apparatus in the presence of 1.5 g of platinum oxide. Hydrogen gas is introduced and the reaction continued until 0.3 mole of hydrogen is consumed. The solution is filtered and the solvent removed in vacuo. The residue is dissolved in ether and an excess of dry HCl bubbled through the solution to yield 4-[(3-ethoxy-2-naphthyl)methyl]piperidine hydrochloride.

EXAMPLE 18

α-(3-Ethoxy-2-naphthyl)-4-piperidinemethanol hydrochloride 13.2 g of 4-[(3-ethoxy-2-naphthyl)methyl]piperidine is stirred with 67 g of potassium t-butoxide in 2.5 l of a 4:1 dimethylsulfoxide-t-butyl alcohol solution under one atmosphere of oxygen at 25° C. for 1 hour. The reaction mixture is added to 4 l of water and the resulting solution extracted with chloroform. The chloroform extract is washed with water, dried over magnesium sulfate and filtered. An excess of dry hydrogen chloride gas is bubbled through the chloroform solution to yield α-(3-ethoxy-2-naphthyl)-4-piperidinemethanol hydrochloride.

EXAMPLE 19

4-[4-(2-Naphthoyl)-1-piperidyl]-1-phenyl-1-butanone hydrochloride

A solution of 16 g (37 mmoles) of 2-naphthyl 4-piperidyl ketone hydrochloride 13 g (71 mmoles) of 4-chloro-1-phenylbutanone, 0.1 g of potassium iodide and 30 g potassium bicarbonate in 100 ml of toluene is heated for 48 hours with stirring on a steam bath. The mixture is partitioned between 100 ml portions of toluene and water and the organic phase dried over MgSO$_4$. A solution of an excess HCl in ether is added and the resulting precipitate recrystallized from methanol/butanone to yield 4-(2-naphthoyl-1-piperidyl)-1-phenyl-1-butanone hydrochloride. M.P. 197°–9°.

EXAMPLE 20

4-[4-(2-Naphthoyl)-1-piperidyl]-1-(4-fluorophenyl)-1-butanone hydrochloride

When in the procedure of Example 19, 4-chloro-1-(4-fluorophenyl)-1-butanone is substituted for 4-chloro-1-phenyl-1-butanone; 4-[4-(2-naphthoyl)-1-piperidyl]-1-(4-fluorophenyl)-1-butanone hydrochloride is produced. M.P. 252°–3°.

EXAMPLE 21

4-[4-(1-Naphthoyl)-1-piperidyl]-1-(4-fluorophenyl)-1-butanone hydrochloride

When in the procedure of Example 19, 4-chloro-1-(4-fluorophenyl)-1-butanone is substituted for 4-chloro-1-phenyl-1-butanone and 1-naphthyl 4-piperidyl ketone hydrochloride is substituted for 2-naphthyl 4-piperidyl ketone hydrochloride, 4-[4-(1-naphthoyl)-1-piperidyl]-1-(4-fluorophenyl)-1-butanone hydrochloride is produced. M.P. 239°–41°.

EXAMPLE 22

3-[4-(4-Bromo-1-naphthoyl)-1-piperidyl]-1-(4-chlorophenyl)-1-propanone hydrochloride When in the procedure of Example 19, 4-bromo-1-naphthyl 4-piperidyl ketone hydrochloride is substituted for 2-naphthyl 4-piperidyl ketone hydrochloride and 3-chloro-1-(4-chlorophenyl)-1-propanone substituted for 4-chloro-1-phenyl-1-butanone, 3-[4-(4-bromo-1-naphthoyl)-1-piperidyl]-1-(4-chlorophenyl)-1-propanone hydrochloride is produced.

EXAMPLE 23

5-[4-(2-Naphthoyl)-1-piperidyl]-1-(4-methylphenyl)-1-pentanone hydrochloride

When in the procedure of Example 19, 5-chloro-1-(4-methylphenyl)-1-pentanone is substituted for 4-chloro-1-phenyl-1-butanone, 5-[4-(2-naphthoyl-1-piperidyl]-1-(4-methylphenyl)-1-pentanone hydrochloride is produced.

EXAMPLE 24

4-[4-(4-Chloro-1-naphthyl)methyl)-1-piperidyl]-1-phenyl-1-butanone hydrochloride When in the procedure of Example 19, 4-[(4-chloro-1-naphthyl)methyl]piperidine hydrochloride is substituted for 2-naphthyl 4-piperidyl ketone hydrochloride, 4-[4-((4-chloro-1-naphthyl)methyl)-1-piperidyl]-1-phenyl-1-butanone hydrochloride is produced.

EXAMPLE 25

4-[4-(6-Chloro-2-naphthoyl)-1-piperidyl]-1-(4-fluorophenyl)-1-butanone

A solution of 3.43 g (12.5 mmoles) of 6-chloro-2-naphthyl 4-piperidyl ketone hydrochloride, 2.63 g (13.1 mmoles) of 4-chloro-1-(4-fluorophenyl)-1-butanone, 2.6 g (26 mmoles) of potassium bicarbonate and a pinch of potassium iodide in 60 ml of toluene is heated at reflux for 80 hours. The mixture is partitioned between toluene and water and the organic phase washed with brine, dried over magnesium sulfate, and concentrated in vacuo to yield 4-[4-(6-chloro-2-naphthoyl)-1-piperidyl]-1-(4-fluorophenyl)-1-butanone.

EXAMPLE 26

4-[4-(6-Chloro-2-naphthoyl)-1-piperidyl]-1-(4-fluorophenyl)-1-butanone methanesulfonate The 4-[4-(6-chloro-2-naphthoyl)-1-piperidyl]-1-(4-fluorophenyl)-1-butanone prepared in Example 25 is dissolved in acetonitrile and 0.6 ml (9.2 mmoles) of methanesulfonic acid added. The mixture is stirred for 5 minutes and concentrated in vacuo and the residue stirred in anhydrous ether for 18 hours. The ether is decanted and the residue recrystallized from butanone and toluene to yield 4-[4-(6-chloro-2-naphthoyl)-1-piperidyl]-1-(4-fluorophenyl)-1-butanone methanesulfonate. M.P. 172°–5°.

EXAMPLE 27

4-[4-((6-Chloro-2-naphthyl)hydroxymethyl)-1-piperidyl]-1-(4-fluorophenyl)-1-butanone When in the procedure of Example 25, α-(6-chloro-2-naphthyl)-4-piperidinemethanol hydrochloride is substituted for 6-chloro-2-naphthyl 4-piperidyl ketone hydrochloride, 4-[4-((6-chloro-2-naphthyl)hydroxymethyl)-1-piperidyl]-1-(4-fluorophenyl)-1-butanone is produced.

EXAMPLE 28

4-[4-((6-Chloro-2-naphthyl)hydroxymethyl)-1-piperidyl]-1-(4-fluorophenyl)-1-butanone methanesulfonate When in the procedure of Example 26, 4-[4-((6-chloro-2-naphthyl)hydroxymethyl)-1-piperidyl]-1-(4-fluorophenyl)butanone is substituted for 4-[4-(6-chloro-2-naphthoyl)-1-piperidyl]-1-(4-fluorophenyl)-1-butanone, 4-[4-((6-chloro-2-naphthyl)hydroxymethyl)-1-piperidyl]-1-(4-fluorophenyl)-1-butanone methanesulfonate is produced.

EXAMPLE 29

4-[4-((2-naphthyl)hydroxymethyl)-1-piperidyl]-1-(4-fluorophenyl)-1-butanone

When in the procedure of Example 25, α-(2-naphthyl)-4-piperidinemethanol hydrochloride is substituted for 6-chloro-2-naphthyl 4-piperidyl ketone hydrochloride and the residual solid recrystallized from chloroform and ethanol, 4-[4-((2-naphthyl)hydroxymethyl)-1-piperidyl]-1-(4-fluorophenyl)butanone is produced. M.P. 100°–102°.

EXAMPLE 30

4-[4-((1-Naphthyl)hydroxymethyl)-1-piperidyl]-1-(4-fluorophenyl)-1-butanone

When in the procedure of Example 25, α-(1-naphthyl)-4-piperidinemethanol hydrochloride is substituted for 6-chloro-2-naphthyl 4-piperidyl ketone hydrochloride, 4-[4-((1-naphthyl)hydroxymethyl)-1-piperidyl]-1-(4-fluorophenyl)-1-butanone is produced. M.P. 172°–4°.

EXAMPLE 31

6-[4-((4-Trifloromethyl-2-naphthyl)methyl)-1-piperidyl]-1-(4-methoxyphenyl)-1-hexanone When in the procedure of Example 25, 4-[(4-trifluoromethyl-2-naphthyl)methyl]piperidine hydrochloride is substituted for 6-chloro-2-naphthyl 4-piperidyl ketone hydrochloride and 6-bromo-1-(4-methoxyphenyl)-1-hexanone substituted for 4-chloro-1-(4-fluorophenyl)-1-butanone, 6-[4-((4-trifluoromethyl-2-naphthyl)methyl)-1-piperidyl]-1-(4-methoxyphenyl)-1-hexanone is obtained.

EXAMPLE 32

α-(4-Fluorophenyl)-4-[(6-chloro-2-naphthyl)hydroxymethyl]-1-piperidinebutanol

When in the procedure of Example 25, α-(6-chloro-2-naphthyl)-4-piperidinemethanol hydrochloride is substituted for 6-chloro-2-naphthyl 4-piperidyl ketone and 4-chloro-1-(4-fluorophenyl)butanol substituted for 4-chloro-1-(4-fluorophenyl)-1-butanone, α-(4-fluorophenyl)-4-[(6-chloro-2-naphthyl)hydroxymethyl]-1-piperidinebutanol is produced.

EXAMPLE 33

α-(4-Fluorophenyl)-4-(6-chloro-2-naphthoyl)-1-piperidinebutanol

When in the procedure of Example 25, 4-chloro-1-(4-fluorophenyl)butanol is substituted for 4-chloro-1-(4-fluorophenyl)-1-butanone, α-(4-fluorophenyl)-4-(6-chloro-2-naphthoyl)-1-piperidinebutanol is obtained.

EXAMPLE 34

α-Phenyl-4-[(3-ethoxy-2-naphthyl)methyl]-1-piperidinepropanol

When in the procedure of Example 25, 4-[(3-ethoxy-2-naphthyl)methyl]piperidine is substituted for 6-chloro-2-naphthyl 4-piperidyl ketone and 3-bromo-1-phenylpropanol substituted for 4-chloro-1-(4-fluorophenyl)-1-butanone, α-phenyl-4-[(3-ethoxy-2-naphthyl)methyl]-1-piperidinepropanol is obtained.

EXAMPLE 35

3-[4-(8-Methyl-1-naphthoyl)-1-piperidyl]-1-(4-fluorophenyl)-1-propanone

A mixture of 25.5 g (0.1 mole) of 8-methyl-1-naphthyl 4-piperidyl ketone, 9 g (0.3 mole) of paraformaldehyde and 13.8 g (0.1 mole) of 4'-fluoroacetophenone in 100 ml of isopropyl alcohol containing 2 drops of concentrated hydrochloric acid is refluxed for 24 hours. The mixture is filtered and the filtrate concentrated to about 100 ml and cooled. The resulting precipitate is recrystallized from ethanol to give 2-[4-(8-methyl-1-naphthoyl)-piperidyl]-1-(4-fluorophenyl)-1-propanone.

EXAMPLE 36

3-[4-((4-Bromo-1-naphthyl)hydroxymethyl)-1-piperidyl]-1-(4-fluorophenyl)-1-propanone When in the procedure of Example 35, α-(4-bromo-1-naphthyl)-4-piperidinemethanol is substituted for 8-methyl-1-naphthyl piperidyl ketone, α-[4-((4-bromo-1-naphthyl)hydroxymethyl)-1-piperidyl]-1-(4-fluorophenyl)-1-propanone is produced.

EXAMPLE 37

α-(4-Fluorophenyl)-4-[(2-naphthyl)hydroxymethyl]-1-piperidinebutanol

To 8.1 g (0.02 mole) of 4-[4-(2-naphthyl)hydroxymethyl)-1-piperidyl]-1-(4-fluorophenyl)-1-butanone HCl in 50 ml of methanol is added 1.1 g (0.02 mole) of sodiummethoxide and then 2.7 g (0.05 mole) of potassium borohydride and the mixture stirred at room temperature for 2 hours. The methanol is removed at reduced pressure on a steam bath after which 50 ml of 10% sodium hydroxide solution is added. The mixture is stirred for 15 minutes and 100 ml of chloroform is added. Stirring is continued for ½ hour. The chloroform layer is separated and combined with two 25 ml chloroform extracts of the aqueous phase, washed with water and with brine, dried over MgSO₄, filtered, and concentrated to a solid. The solid material is recrystallized from ethanol/water to give α-(4-fluorophenyl)-4-[(2-naphthyl)hydroxymethyl]-1-piperidinebutanol.

EXAMPLE 38

α-Phenyl-4-[(4-chloro-1-naphthyl)methyl]-1-piperidinebutanol

When the procedure of Example 37, 4-[4-((4-chloro-1-naphthyl)methyl)-1-piperidyl]-1-phenyl-1-butanone hydrochloride is substituted for 4-[4-(2-naphthyl)hydroxymethyl)-1-piperidyl]-1-(4-fluorophenyl)-1-butanone, α-phenyl-4-[(4-chloro-1-naphthyl)methyl]-1-piperidinebutanol is obtained.

EXAMPLE 39

α-(4-Fluorophenyl)-4-[(6-chloro-2-naphthyl)hydroxymethyl]-1-piperidinebutanol

To a stirred suspension of 4.4 g (0.01 mole) of 4-[4-(6-chloro-2-naphthoyl)-1-piperidyl]-1-(4-fluorophenyl)-1-butanone in 100 ml of absolute ethanol at 50° C. is gradually added 1.9 g (0.05 mole) sodium borohydride. Stirring is continued at 50° for one hour after the addition is completed and 20 ml of 3 N hydrochloric acid is added slowly. The mixture is diluted to 400 ml with water, made basic with sodium hydroxide, and extracted with chloroform. The organic phase is dried over MgSO₄, concentrated in vacuo and recrystallized to yield α-(4-fluorophenyl)-4-[(6-chloro-2-naphthyl)hydroxymethyl]-1-piperidinebutanol.

EXAMPLE 40

α-(4-Fluorophenyl)-4-[(8-methyl-1-naphthyl)hydroxymethyl]-1-piperidinepropanol

When in the procedure of Example 39, 3-[4-(8-methyl-1-naphthoyl)-1-piperidyl]-1-(4-fluorophenyl)-1-propanone is substituted for 4-[4-(6-chloro-2-naphthoyl)-1-piperidyl]-1-(4-fluorophenyl)-1-butanone, α-(4-fluorophenyl)-4-[(8-methyl-1-naphthyl)hydroxymethyl]-1-piperidinepropanol is obtained.

EXAMPLE 41

Tablet Formulation

An illustration of a representative tablet formulation of an active compound of this invention is as follows:

| | Per Tablet |
|---|---|
| (a) 4-[(4-(1-naphthyl)hydroxymethyl)-1-piperidyl]-1-(4-fluorophenyl)-1- | |

| | Per Tablet |
|---|---|
| butanone | 25.0 mg |
| (b) Wheat starch | 3.5 mg |
| (c) Lactose | 10.0 mg |
| (d) Magnesium Stearate | 0.5 mg |

A granulation obtained upon mixing lactose with the starch and granulated starch paste is dried, screened and mixed with the active ingredient and magnesium stearate. The mixture is compressed into tablets weighing 39.0 mg each.

EXAMPLE 42

Gelatin Capsule Formulation

An illustrative composition for hard gelatin capsules is as follows:

| | Mg |
|---|---|
| (a) 4-[(4-(2-naphthoyl)-1-piperidyl]-1-(4-fluorophenyl)-1-butanone hydrochloride | 10 |
| (b) Talc | 5 |
| (c) Lactose | 100 |

The formulation is prepared by passing the dry powders of (a) and (b) through a fine mesh screen and mixing them well. The powder is then filled into hard gelatin capsules at a net fill of 115 mg per capsule.

EXAMPLE 43

Injectable Suspension Formulation

An illustrative composition for an injectable suspension is the following 1 ml ampul for an intramuscular injection.

| | Weight Percent |
|---|---|
| (a) 4-[(4-(1-naphthyl)hydroxymethyl)-1-piperidyl]-1-(4-fluorophenyl)-1-butanone (particle size <10μ) | 1.0 |
| (b) Polyvinylpyrrolidone (M.W. 25000) | 0.5 |
| (c) Lecithin | 0.25 |
| (d) Water for injection to make | 100.0 |

The materials (a)–(d) are mixed, homogenized, and filled into 1 ml ampuls which are sealed and autoclaved 20 minutes at 121° C. Each ampul contains 10 mg per ml of novel compound (a).

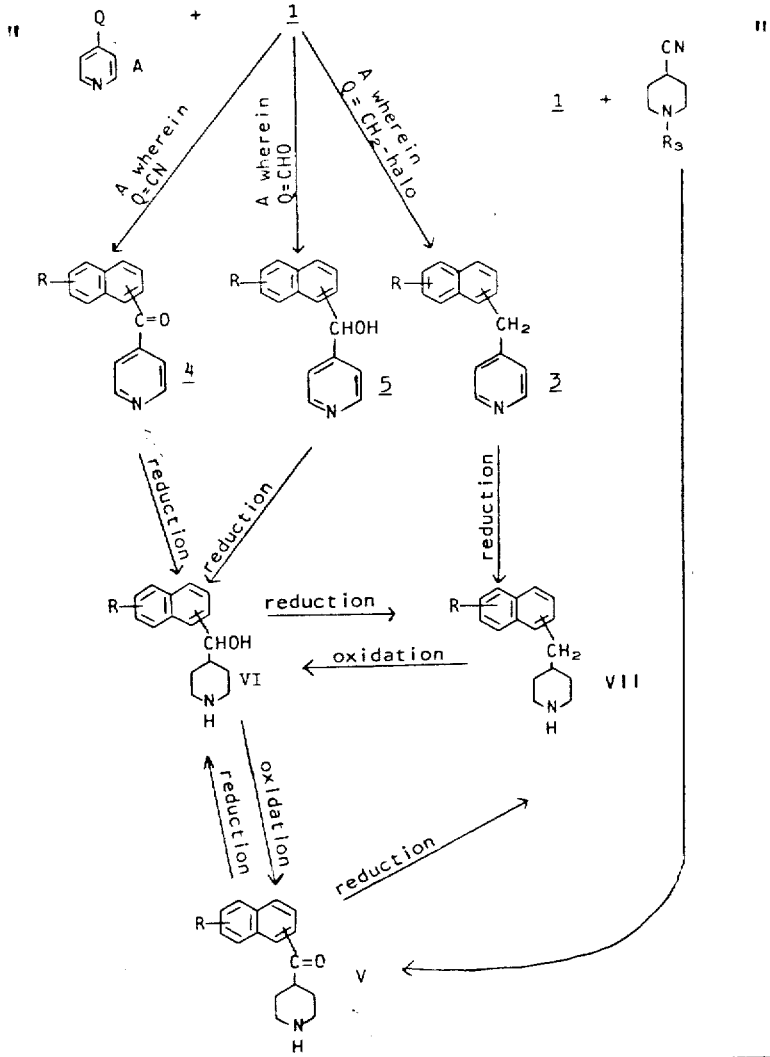

I claim:

1. A compound of the formula

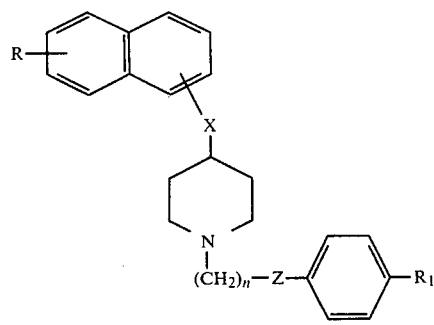

wherein n is an integer of from 2 to 5; R is selected from hydrogen, halogen, straight or branched chain alkyl of from 1 to 4 carbon atoms, straight or branched chain alkoxy of from 1 to 4 carbon atoms and trifluoromethyl; $R_1$ is selected from hydrogen, halogen, straight or branched alkyl of from 1 to 4 carbon atoms, and straight or branched alkoxy of from 1 to 4 carbon atoms; X is selected from carbonyl, hydroxymethlene and methylene; and Z is selected from carbonyl and hydroxymethylene; an individual diastereomer or optical isomer, or a pharmaceutically acceptable acid addition salt thereof.

2. A compound of claim 1 wherein Z is carbonyl.

3. A compound of claim 1 wherein Z is hydroxymethylene.

4. A compound of claim 1 wherein X is selected from carbonyl and hydroxymethylene.

5. A compound of claim 1 wherein n is 3.

6. A compound of claim 1 wherein $R_1$ is halogen.

7. A compound of claim 6 wherein $R_1$ is fluorine.

8. A compound of claim 1 wherein R is selected from hydrogen and halogen.

9. A compound of claim 1 which is 4-[4-(2-naphthoyl)-1-piperidyl]-1-(4-fluorophenyl)-1-butanone or a pharmaceutically acceptable acid addition salt thereof.

10. A compound of claim 1 which is 4-[4-(1-naphthyl)hydroxymethyl)-1-piperidyl]-1-(4-fluorophenyl)-1-butanone or a pharmaceutically acceptable acid addition salt thereof.

11. A compound of claim 1 which is 4-[4-(1-naphthoyl)-1-piperidyl]-1-(4-fluorophenyl)-1-butanone.

12. A compound of claim 1 which is 4-[4-(6-chloro-2-naphthoyl)-1-piperidyl]-1-(4-fluorophenyl)-1-butanone or a pharmaceutically acceptable acid addition salt thereof.

13. An antipsychotic composition comprising an antipsychotically effective amount of a compound of claim 1 and a pharmaceutical carrier.

14. A composition of claim 13 comprising from 0.5 to 200 mg of the compound in unit dosage form.

15. A method of obtaining tranquilizing effects in a patient in need thereof comprising administering to said patient a tranquilizing amount of a compound of claim 1.

16. The method of claim 15 wherein the compound is administered in a dosage of from 0.005 to 100 mg per kg of body weight of the patient per day.

17. The method of claim 15 wherein the compound is 4-[4-(2-naphthoyl)-1-piperidyl]-1-(4-fluorophenyl)-1-butanone or a pharmaceutically acceptable acid addition salt thereof.

18. The method of claim 15 wherein the compound is 4-[4-((1-naphthyl)hydroxymethyl)-1-piperidyl]-1-(4-fluorophenyl)-1-butanone or a pharmaceutically acceptable acid addition salt thereof.

19. A compound of the formula

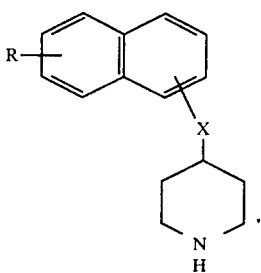

wherein R is selected from hydrogen, halogen, straight or branched chain alkyl of from 1 to 4 carbon atoms, straight or branched chain alkoxy of from 1 to 4 carbon atoms and trifluoromethyl and X is selected from carbonyl, hydroxymethylene and methylene, with the proviso that when X is carbonyl or hydroxymethylene, R is other than hydrogen or alkyl; an individual optical isomer, or an acid addition salt thereof.

20. A compound of claim 19 wherein X is carbonyl or an acid addition salt thereof.

21. A compound of claim 19 wherein X is hydroxymethylene or an acid addition salt thereof.

22. A compound of claim 19 wherein X is methylene or an acid addition salt thereof.

23. A compound of claim 19 which is 6-chloro-2-napthyl 4-piperidyl ketone or an acid addition salt thereof.

* * * * *

UNITED STATES PATENT AND TRADEMARK OFFICE
CERTIFICATE OF CORRECTION

PATENT NO. : 4,246,268

DATED : January 20, 1981

INVENTOR(S) : Albert A. Carr

It is certified that error appears in the above—identified patent and that said Letters Patent is hereby corrected as shown below:

Columns 13 and 14, lines 1-60 should be cancelled and the attached sheet substitute therefor.

Signed and Sealed this

Seventeenth Day of November 1981

[SEAL]

Attest:

Attesting Officer

GERALD J. MOSSINGHOFF

Commissioner of Patents and Trademarks

UNITED STATES PATENT AND TRADEMARK OFFICE
CERTIFICATE OF CORRECTION

PATENT NO. : 4,246,268

DATED : January 20, 1981

INVENTOR(S) : Albert A. Carr

It is certified that error appears in the above—identified patent and that said Letters Patent is hereby corrected as shown below: